United States Patent [19]
Velan et al.

[11] Patent Number: 4,877,865
[45] Date of Patent: Oct. 31, 1989

[54] BOVINE INTERFERON

[75] Inventors: Baruch Velan, Rishon Le-Zion; Sara Cohen, Bat-Yam; Haim Grosfeld, Rehovot; Avigdor Shafferman, Ness-Ziona, all of Israel

[73] Assignee: State of Israel, Prime Minister's Office, Israel Institute for Biological Research, Nes Ziona, Israel

[21] Appl. No.: 721,204

[22] Filed: Apr. 9, 1985

[30] Foreign Application Priority Data

Apr. 15, 1984 [IL] Israel ......................................... 71555

[51] Int. Cl.$^4$ ...................... C07K 13/00; C07K 15/26; A61K 45/02; C12P 21/00
[52] U.S. Cl. .................................... 530/351; 424/85.7; 435/68
[58] Field of Search ....................... 424/85, 85.4, 85.7; 530/351; 435/68, 811

[56] References Cited

U.S. PATENT DOCUMENTS 4,289,690 9/1981 Pestka et al. ........................ 435/811

FOREIGN PATENT DOCUMENTS

80/02375 11/1980 PCT Int'l Appl. .
2116566 9/1983 United Kingdom .

Primary Examiner—Blondel Hazel
Attorney, Agent, or Firm—Bucknam and Archer

[57] ABSTRACT

There is provided genetically engineered bovine interferon of the IFN-α-type and various sub-types thereof. There is further provided a double stranded DNA molecule which includes DNA encoding BoIFN-α A, BoIFN0α B, BoIFN-α C, and BoIFN-α D, and cloning vehicles including such DNAs. There are further provided cells including such DNA and a process for the production of such types of BoIFN based on the use of such cells. Furthermore, there is also provided a method for the identification of a bovine IFN-α DNA sequence.

12 Claims, 7 Drawing Sheets

CTGAAGGAAGGTCTTCAGAGAACCTAGAGAGCAGGTTCACAGAGTCACCCACCTCACCAG

GCCAAAGCATCTGCAAGGTCCCCGATGGCCCCAGCCTGGTCCTTCCTGCTATCCCTGTTG
                             MetAlaProAlaTrpSerPheLeuLeuSerLeuLeu

CTGCTCAGCTGCAACGCCATCTGCTCTCTGGGTTGCCACCTGCCTCACACCCACAGCCTG
LeuLeuSerCysAsnAlaIleCysSerLeuGlyCysHisLeuProHisThrHisSerLeu

GCCAACAGGAGGGTCCTGATGCTCCTGCAACAACTGAGAAGGGTCTCCCCTTCCTCCTGC
AlaAsnArgArgValLeuMetLeuLeuGlnGlnLeuArgArgValSerProSerSerCys

CTGCAGGACAGAAATGACTTCGAATTCCTCCAGGAGGCTCTGGGTGGCAGCCAGTTGCAG
LeuGlnAspArgAsnAspPheGluPheLeuGlnGluAlaLeuGlyGlySerGlnLeuGln

AAGGCTCAAGCCATCTCTGTGCTCCACGAGGTGACCCAGCACACCTTCCAGCTCTTCAGC
LysAlaGlnAlaIleSerValLeuHisGluValThrGlnHisThrPheGlnLeuPheSer

ACAGAGGGCTCGCCCGCCACGTGGGACAAGAGCCTCCTGGACAAGCTACGCGCTGCGCTG
ThrGluGlySerProAlaThrTrpAspLysSerLeuLeuAspLysLeuArgAlaAlaLeu

GATCAGCAGCTCACTGACCTGCAAGCCTGTCTGACGCAGGAGGAGGGGCTGCGAGGGGCT
AspGlnGlnLeuThrAspLeuGlnAlaCysLeuThrGlnGluGluGlyLeuArgGlyAla

CCCCTGCTCAAGGAGGACTCCAGCCTGGCTGTGAGGAAATACTTCCACAGACTCACTCTC
ProLeuLeuLysGluAspSerSerLeuAlaValArgLysTyrPheHisArgLeuThrLeu

TATCTGCAAGAGAAGAGACACAGCCCTTGTGCCTGGGAGGTTGTCAGAGCAGAAGTCATG
TyrLeuGlnGluLysArgHisSerProCysAlaTrpGluValValArgAlaGluValMet

AGAGCCTTCTCTTCCTCAACAAACTTGCAGGAGAGTTTCAGGAGAAAGGACTGACACACA
ArgAlaPheSerSerSerThrAsnLeuGlnGluSerPheArgArgLysAspEND

CCTGGTCCAACACGGAAA

FIG. 1

```
                          TGAACCCATTTGGAGAGTGCAAGCTGAAACGCAAAAACAAAAGT

AGAAAACAAGAGGGAACTTTCACAAAGTGGAAACCATGGGCTCCTATTTAAGACACAGGC

CTGAAGGAAGGTCTTCAGAGAATCTAGAGAGCAGGTTCACAGAGTCACCCACCGCCCGAG

GCCAAAGCCTCTGCAAGGTCCCCGATGGCCCCAGCCTGGTCCTTCCTCCTAGCCCTGCTG
                         MetAlaProAlaTrpSerPheLeuLeuAlaLeuLeu
                                                  ▼
CTGCTCAGCTGCAACGCCATCTGCTCTTTGGGTTGCCACCTGCCTCACACCCACAGCCTG
LeuLeuSerCysAsnAlaIleCysSerLeuGlyCysHisLeuProHisThrHisSerLeu

CCCAACAGGAGGGTCCTGACACTCCTGCGACAACTGAGGAGGGTCTCCCCTTCCTCCTGC
ProAsnArgArgValLeuThrLeuLeuArgGlnLeuArgArgValSerProSerSerCys

CTGCAGGACAGAAATGACTTTGCATTCCCCCAGGAGGCGCTGGGTGGCAGCCAGTTGCAG
LeuGlnAspArgAsnAspPheAlaPheProGlnGluAlaLeuGlyGlySerGlnLeuGln

AAGGCTCAAGCCATCTCTGTGCTCCACGAGGTCACCCAGCACACCTTCCAGCTCTTCAGC
LysAlaGlnAlaIleSerValLeuHisGluValThrGlnHisThrPheGlnLeuPheSer

ACAGAGGGCTCGGCCACTACGTGGGACGAGAGCCTCCTGGACAAGCTCCACGCTGCACTG
ThrGluGlySerAlaThrThrTrpAspGluSerLeuLeuAspLysLeuHisAlaAlaLeu

GATCAGCAGCTCACTGACCTGCAAGCCTGTCTGAGGCAGGAGGAGGGGCTGCGAGGGGCT
AspGlnGlnLeuThrAspLeuGlnAlaCysLeuArgGlnGluGluGlyLeuArgGlyAla

CCCCTGCTCAAGGAGGGTTCCAGCCTGGCTGTGAGGAAATACTTCCACAGACTCACTCTC
ProLeuLeuLysGluGlySerSerLeuAlaValArgLysTyrPheHisArgLeuThrLeu

TATCTGCAAGAGAAGAGACACAGCCCTTGTGCCTGGGAGGTTGTCAGAGCAGAAGTCATG
TyrLeuGlnGluLysArgHisSerProCysAlaTrpGluValValArgAlaGluValMet

AGAGCCTTCTCTTCTTCAACAAACTTGCAGGAGAAATTCAGGAGAAAGGACTGACACACA
ArgAlaPheSerSerSerThrAsnLeuGlnGluLysPheArgArgLysAspEND

CCTGGTTCAACATGGAAA
```
FIG. 2

AGAAAGCAAGAGGGAACTTTCAGAAAATGGAAACCATGGGCTCCTATTTAACACACAGGC

CTGAAGGAAGGTCTTCAGAGAACCTAGAAAGCAGGTTCACAGAGTCACCCACCTCCCCAG

GCCACAGCATCTGCAAGGTCCCCAATGGCCCCAGCCTGGTCCTTCCGCCTGGCCCTGCTG
                              MetAlaProAlaTrpSerPheArgLeuAlaLeuLeu

CTGCTCAGCTGCAATGCCATCTGCTCTCTGGGCTGCCACCTGCCTCACACCCACAGCCTG
LeuLeuSerCysAsnAlaIleCysSerLeuGlyCysHisLeuProHisThrHisSerLeu

GCCAACAGGAGGGTCCTGATGCTCCTGGGACAACTGAGGAGGGTCTCCCCTTCCTCCTGC
AlaAsnArgArgValLeuMetLeuLeuGlyGlnLeuArgArgValSerProSerSerCys

CTGCAGGACAGAAATGACTTTGCATTCCCCCAGGAGGCGCTGGGTGGCAGCCAGTTGCAG
LeuGlnAspArgAsnAspPheAlaPheProGlnGluAlaLeuGlyGlySerGlnLeuGln

AAGGCTCAAGCCATCTCTGTGCTCCACGAGGTGACCCAGCACACCTTCCAGCTTTTCAGC
LysAlaGlnAlaIleSerValLeuHisGluValThrGlnHisThrPheGlnLeuPheSer

ACAGAGGGCTCGGCCACCATGTGGGATGAGAGCCTCCTGGACAAGCTCCGCGATGCACTG
ThrGluGlySerAlaThrMetTrpAspGluSerLeuLeuAspLysLeuArgAspAlaLeu

GATCAGCAGCTCACTGACCTGCAATTCTGTCTGAGGCAGGAGGAGGAGCTGCAAGGAGCT
AspGlnGlnLeuThrAspLeuGlnPheCysLeuArgGlnGluGluGluLeuGlnGlyAla

CCCCTGCTCAAGGAGGACTCCAGCCTGGCTGTGAGGAAATACTTCCACAGACTCACTCTC
ProLeuLeuLysGluAspSerSerLeuAlaValArgLysTyrPheHisArgLeuThrLeu

TATCTGCAAGAGAAGAGACACAGCCCTTGTGCCTGGGAGGTTGTCAGAGCACAAGTCATG
TyrLeuGlnGluLysArgHisSerProCysAlaTrpGluValValArgAlaGlnValMet

AGAGCCTTCTCTTCCTCAACAAACTTGCAGGAGAGTTTCAGGAGAAAGGACTGACACACA
ArgAlaPheSerSerSerThrAsnLeuGlnGluSerPheArgArgLysAspEND

CCTGGTTCAACACGGAAATGATTCTCATGGACCAACAGACCACACTTCCTCCTGCGCTGC

CATGTGGAAGATTCATTTCTGCTGTCATCAGGCACTGAACTGAATCAATTTGTTAAATGA

FIG. 3

AGAAAGCAAGAGGGAACTTTCAGAAAATGGAAACCATGGACTCCTATTTAAGACACAGAC

CTGAAGGAAGGTCTTCAGAGAACCTAGAAAGCAGGTTCACAGAGTCACCCACCGCCCCAG

GCCACAGCCACTTCAAGGTCCCCGATGGCCCCAGCCTGGTCCCTCCTCCTGGCTCTGCTG
                              MetAlaProAlaTrpSerLeuLeuLeuAlaLeuLeu

CTGCTCAGCTGCAACGCCATCTGCTCTCTGGGCTGCCACCTGCCTCACTCCCACAGCCTG
LeuLeuSerCysAsnAlaIleCysSerLeuGlyCysHisLeuProHisSerHisSerLeu

GCCAAGAGGAGAGTCCTGACACTCCTGCGACAACTGAGGAGGGTCTCCCCTTCCTCCTGC
AlaLysArgArgValLeuThrLeuLeuArgGlnLeuArgArgValSerProSerSerCys

CTGCAGGACAGAAATGACTTCGCATTCCCCCAGGAGGCGCTGGGTGGCAGCCAGTTGCAG
LeuGlnAspArgAsnAspPheAlaPheProGlnGluAlaLeuGlyGlySerGlnLeuGln

AAGGCTCAAGCCATCTCTGTACTCCACGAGGTGACCCAACACACCTTCCAGCTTTCCAGC
LysAlaGlnAlaIleSerValLeuHisGluValThrGlnHisThrPheGlnLeuSerSer

ACAGAGGGCTCGGCCGCTGTGTGGGATGAGAGCCTCCTGGACAAGCTCCGCACTGCACTG
ThrGluGlySerAlaAlaValTrpAspGluSerLeuLeuAspLysLeuArgThrAlaLeu

GATCAGCAGCTCACTGACCTGCAAGCCTGTCTGAGGCAGGAGGAGGGGCTGCCAGGGGCT
AspGlnGlnLeuThrAspLeuGlnAlaCysLeuArgGlnGluGluGlyLeuProGlyAla

CCCCTGCTCAAGGAGGACTCCAGCCTGGCTGTGAGGAAATACTTCCACAGACTCACTCTC
ProLeuLeuLysGluAspSerSerLeuAlaValArgLysTyrPheHisArgLeuThrLeu

TATCTGCAAGAGAAGAGACACAGCCCTTGTGCCTGGGAGGTTGTCAGAGCACAAGTCATG
TyrLeuGlnGluLysArgHisSerProCysAlaTrpGluValValArgAlaGlnValMet

AGAGCCTTCTCTTCCTCAACAAACTTGCAGGAGAGATTCAGGAGAAAGGACTGACACACA
ArgAlaPheSerSerSerThrAsnLeuGlnGluArgPheArgArgLysAspEND

CCTGGTTCAACACGGAAATGATTCTCACGGACCAACAGACCACACTTCCTCCTGCGCTGC

CATGTGGAAGACTCATTTCTGCTGTCATCAGGCACTGAACTGAATCAATTTGTTAATGGT

FIG. 4

```
            S1               S20   1                 20                  40
BoIFN- C    MAPAWSFRLALLLLSCNAICSLGCHLPHTHSLANRRVLMLLGQLRRVSPSSCLQDRNDFAFPQ
BoIFN- A           L S                               Q                 E L
BoIFN- B           L                        P     T  R
BoIFN- D          LL                    S    K    T  R 60                  80                 100
BoIFN- C    EALGGSQLQKAQAISVLHEVTQHTFQLFSTEGSATMWDESLLDKLRDALDQQLTDLQFCLRQE
BoIFN- A                                     PAT  K       A          A T
BoIFN- B                                       T         HA          A
BoIFN- D                               S      AV          T          A 120                 140                 160
BoIFN- C    EELQGAPLLKEDSSLAVRKYFHRLTLYLQEKRHSPCAWEVVRAQVMRAFSSSTNLQESFRRKD
BoIFN- A     G R                                       E
BoIFN- B     G R       G                               E             K
BoIFN- D     G P                                                     R
```

BOVINE INTERFERON

BACKGROUND OF THE INVENTION

Interferons are a family of proteins or glycoproteins produced by cells in response to viral infections or other inducing agents, such as double-stranded RNA or mitogens. Interferons are released from the producing cells and interact with other cells to confer on them a broad antiviral resistance. In addition, they inhibit cell proliferation and modulate the immune response (Stewart W. E., 1979, The Interferon System, Springer).

Interferons, produced by different cells, were found to differ in their physicochemical, serological and functional properties. Human interferons are now grouped into three categories—α, β, and γ, based on their antigenic specificities; a similar classification can be applied to murine interferons.

In order to limit economical losses provoked by viral diseases of cattle, the availability of an antiviral agent of a wide spectrum of action is of importance. High morbidity is observed under certain circumstances, such as transport of animals or their regroupment in a new environment, where they are confronted with new viral infections. Prophylactic or therapeutic use of bovine interferons seem to be ideal in these circumstances.

The bovine interferons (BoIFN), unlike their counterparts from human or murine sources, have not been extensively studied. BoIFN are likely to be a potent agent for the prevention of virus mediated cattle diseases such as Foot and Mouth Disease, Infectious Bovine Rhinotracheitis, Pseudorabies, Bluetongue and Neonatal Bovine Diarrhea. When BoIFN preparations were tested in vitro, they exerted antiviral activity against some of the viruses involved in these diseases (Goossens, A et al Ann. Met. Vet. 127 p. 135 1983).

α-Interferons are a family of related proteins coded by over a dozen distinct genes. This was demonstrated in mice, humans and now as shown by us also in cattle. (Goeddel D. U. et al 1981 Nature 290 20; Nagata S et al 1980, Nature 287,401; Shaw et al 1983, Nuc. Acid. Res. 11 555; Wilson et al 1983 J. Mol. Biol. 166, 457). The IFNα genes have substantial sequence homology, yet they are conserved throughout the evolution. It is therefore believed that differential in vivo production of appropriate interferons is required for a successful defensive response in humans to specific viral infections, immunological interferences and neoplastic disorders.

The major obstacle for a clinical evaluation of predetermined combination of α-interferon preparations stems from the difficulties in obtaining large quantities of the purified proteins of each one of the interferon types. The techniques of genetic engineering provided the tools for obtaining a reliable source for the production of individual IFNα proteins. These techniques allow one to isolate the genetic information of each interferon, by direct manipulation of the genome or its transcription products, or by chemical synthesis of the complete IFNα coding sequence, and to clone this information in prokaryotic or eukaryotic cells. Further manipulations of these individual IFN sequences together with appropriate expression signals (transcription and translation signals) lead to high levels of production of the cloned interferons.

SUMMARY OF THE INVENTION

The major object of this invention is to provide a source for the production of novel distinct products of the bovine interferon-α protein series, and to the essentially pure kinds of interferon-α thus produced.

FIG. 1 illustrates the nucleotide sequence of the BoIFN-α A gene and the corresponding amino acid sequence of: pre-BoIFN-α A and of mature-BoIFN-αA; in Met-mature-BoIFN-αA, a methionine codon (at the position indicated by the black triangle) precedes the Cys codon.

FIG. 2 illustrates the nucleotide sequence of the BoIFN-α B gene and the corresponding amino acid sequence of: pre-BoIFNα B and of mature-BoIFN-αB in Met-mature-BoIFN-αB, a methionine codon (at the position indicated by the black triangle) precedes the Cys codon.

FIG. 3 illustrates the nucleotide sequence of the BoIFN-α C gene and the corresponding amino acid sequence of: pre BoIFN-α C and of mature-BoIFN-α C; in Met-mature-BoIFn-αC, a methionine codon (at the position indicated by the black triangle) precedes the Cys codon.

FIG. 4 illustrates the nucleotide sequence of the BoIFN-D gene and the corresponding amino acid sequence of: pre-BoIFNα D and of mature-BoIFN-α D; in Met-mature-BoIFN-αD, a methionine codon (at the position indicated by the black triangle) preceds the Cys codon.

FIG. 5 shows a comparison of amino acid sequence of the BoIFN-α A, αB, αC and αD; mature BoIFN sequence starts from amino acid 1 (Cys) while the pre-BoIFN contains in addition the signal peptide of 23 amino acids (numbers of signal amino acids are preceded by the letter S). Only differences from BoIFN-α C are shown in the Figures.

A. Steps involved in the insertion of the bovine IFN-αC sequences in the trp expression vehicle pSE2: The open bar represents the 360 bp trp E. coli promoter fragment containing the first 6 codons of the trpL. Shaded bar represents 525 bp of the coding sequences of the BoIFN-αC. The insertion of the bovine Pvu II-—Sma I DNA fragment in the filled-in EcoRI site of pSE2 regenerates the EcoRI site.

B. N-terminal sequences of the fused trpL-BoIFN-αC (f-BoIFN-αC) polypeptide.

Figure 7:
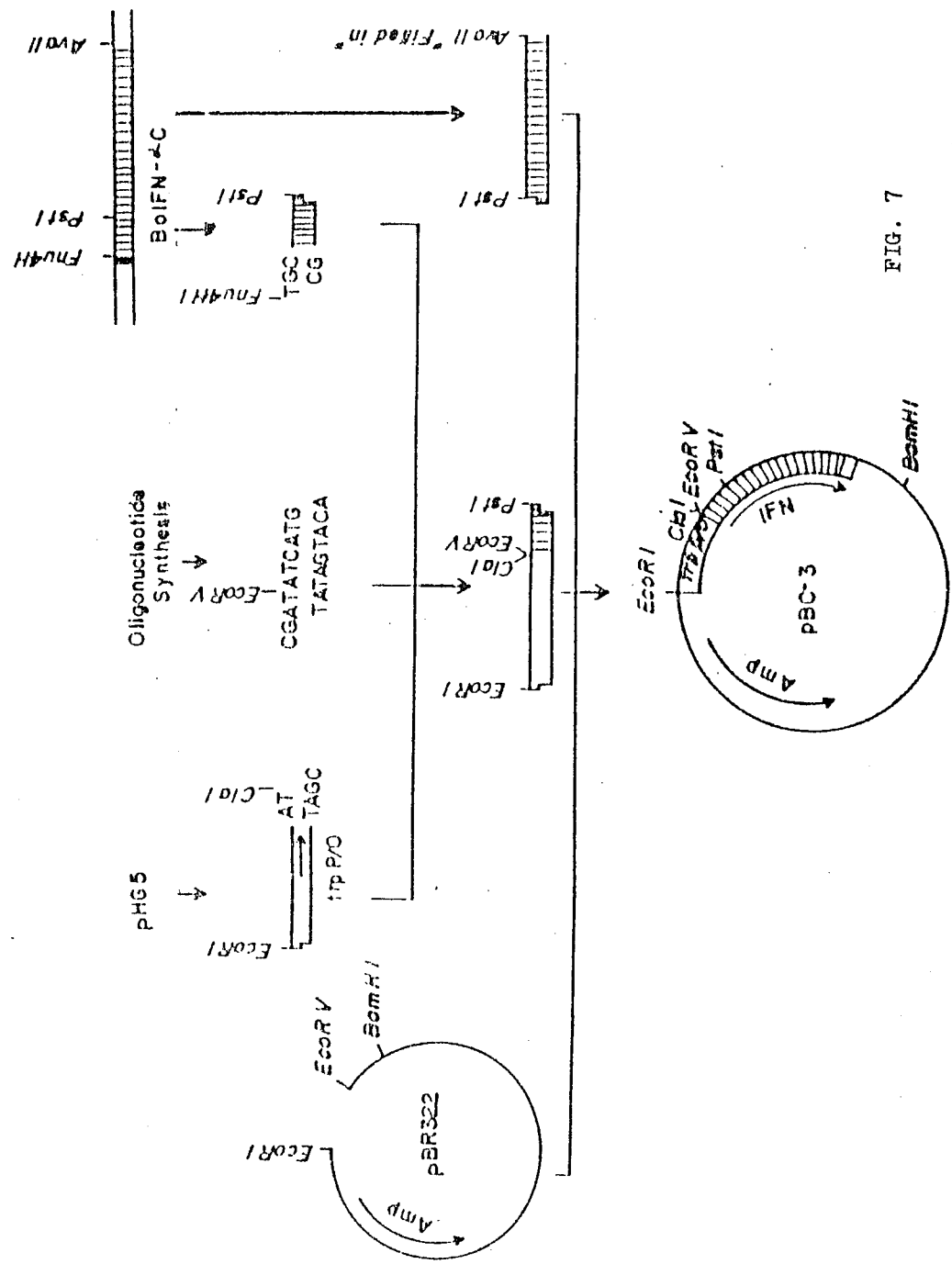

FIG. 7 illustrates the construction of pBC-3 for the expression of mature met-BoIFN-αC. Shaded areas mark coding region for mature-BoIFN-αC. Black areas mark signal peptide sequences.

The isolation, cloning and expression of the bovine interferon-α genes comprise the following steps:

a. Construction of a bovine genomic library using phage λ vectors:
  1. Isolation, purification and partial digestion of bovine DNA from bovine tissues such as liver; Isolation of 12–20 kb DNA fragments,
  2. Preparation of λ DNA vector arms, such as λ L47.1 arms, and ligation of the arms to the fractionated bovine DNA fragments,
  3. Packaging and amplification of the λ hybrids to form the bovine genomic library.

b. Isolation of BoIFN-α genes;
  1. Preparation of specific probes for BoIFN-α genes: Isolation of HuIFN-α, cDNA sequences covering the entire coding region of the gene and radioactive labelling of these DNA probes.
2. Determination of screening conditions for the genomic library using HuIFN-α probe hybridization to bovine genomic blotts.
3. Screening of the genomic library by in situ hybridization.
4. Plaque purification of positive clones and isolation of λ hybrid phage DNA.
5. Restriction map analysis of the λ hybrid clones and location of DNA regions homologous to HuIFN-α.
c. Sequence analysis of the BoIFNα genes.
d. Subcloning of the BoIFNα genes for expression in heterologous systems such as bacteria or eukaryotic cells.
   1. Fragmentation of λ hybrid DNA sequences by restriction enzymes. Isolation of BoIFNα coding sequences.
   2. Preparation of expression vehicles and synthetic oligonucleotides for construction of DNA elements expressing high levels of the BoIFN-α polypeptide in vivo.
e. Production and Purification of BoIFN-α and its derivatives.

Total DNA is extracted from bovine cells such as liver, placenta and thymus cells. DNA is extracted from the cells by extraction procedures using reagents such as phenol. The DNA is randomly fragmented by mechanical shearing or by digestion with restriction enzymes. Partially digested or sheared DNA is fractionated by methods such as sucrose density gradient centrifugation or gel electrophoresis to obtain fragments of the required size. These fragments are inserted into cloning vehicles to construct the genomic library.

The choice of vector is influenced by many factors including the type of foreign DNA being inserted, the type of restriction endonuclease used, whether or not expression of the insert is required, and the nature of the host. Commonly used vectors are cosmids, bacteriophages or plasmids that have a number of useful restriction endonuclease sites, and a means of identifying bacteria that carry a recombinant DNA molecule. Viral vectors have the advantage that they infect cells with high efficiency and reproduce rapidly. One further unique advantage of phage vectors is that their DNA is completely packaged in the virus particle and therefore the foreign DNA can be stored and amplified easily. The latter property is very useful when one has to manipulate a library of over one million different clones.

The genomes of the entire family of lambdoid phages are organized so that their central one-third (stuffer segment) contains genes that are entirely dispensable for lytic growth.

The essential right and left ends of the phage are designated right and left arms. The non-essential sequences can be deleted using various restriction enzymes. These cloning vehicles allow the insertion of 15 to 20 kb of foreign DNA between the phage arms. In practice the bacteriophage λ vector DNA is first treated with a restriction enzyme and then the arms are separated from the middle "stuffer segment". The isolated arms are then ligated with the chromosomal DNA of interest. Depending on the vector used, any of several approaches for "arms preparation" may be used. The sucrose density gradient centrifugation proved to be the most efficient one and is the method of choice in the present study.

Cloning of the hybrid phages was based on the in vitro packaging system (Hohn B 1975, J. Mol. Bio 98, 93). The in vitro packaged DNA was propagated in $E.$ $coli$ cells, thus establishing the recombinant phage library which represent the entire genome. Several such libraries were amplified and used as a source for isolation of bovine genes.

To isolate a single gene from a library of a eukaryotic DNA ($3 \times 10^9$ bp genome size), one has to screen more than 100,000 clones assuming an average size of 20 kb for the eukaryotic inserts. A screening procedure which allows one to handle such a large collection of clones is provided by hybridization in-situ, if a labelled sequence-specific probe for the desired gene is available. Since we had no prior knowledge of the bovine IFN sequence, we decided to use the human IFNα sequences which we had cloned previously (Interferon Production, Israel patent application No. 70678, 1984) to probe the bovine library for BoIFN-α genes. Before using the HuIFN sequences as probes for the bovine library, it was confirmed that the HuIFN sequence can hybridize specifically to bovine DNA by genomic blotts.

λ clones which hybridize with the HuIFN-α probe are isolated, propagated and their DNA analyzed by restriction enzyme digestion and southern blotts to map locate the regions homologous to HuIFN-α DNA. Extensive restriction enzyme analysis of this DNA region allows further genetic manipulation of the BoIFN-α gene. 13 clones hybridizing specifically with HuIFN-α probe were identified so far. These represent at least 5 distinct members of the BoIFN-α gene family, four of which were further analyzed and their complete DNA sequence was determined (FIGS. 1, 2, 3, 4).

To evaluate the biological activity of the BoIFN-α, an efficient expression vehicle can be used for the production of the BoIFN-α, polypeptide or the mature met-IFN polypeptide.

For efficient expression in bacteria of BoIFN-α genes plasmids were constructed which included efficient transcription promoters such as lac, trp, λ$P_L$ or λ$P_R$ together with natural or synthetic bacterial efficient translation initiation signals and the appropriate coding sequences which eventually lead to the production of the met-IFN polypeptide.

The BoIFNα genes can be manipulated also for efficient expression in eukaryotic cells where they will be cloned with the natural signal peptide coding sequences which will be processed in vivo and thus produce the authentic natural IFNα polypeptide.

Furthermore, the BoIFNα sequences can be manipulated in such a way that a fused polypeptide will be produced in the bacterial or eukaryotic cell and the fused polypeptide will be further processed by the cells or in vitro to produce the authentic natural IFN-α polypeptide.

BoFIN-α can be produced in a eukaryotic or prokaryotic carrier based on the specific expression regulation system which was constructed. For example, expression in prokaryotes using the trp transcription promoter can be induced by controlling tryptophan concentration in the growth medium, alternatively production can be made constitutive either by introduction into a trp repressor defective strain or by a construction using a trp operator constitutive mutant.

Growth under the appropriae conditions as described above leads to accumulation of the genetically engineered BoIFNα polypeptide. The IFN extraction step depends on whether or not the product is extra- or intracellular. For the latter procedures involving cell membrane disruption with enzymes, detergents or mechanical force are used. The purification procedure is based on the physicochemical, immunological and biological properties of the BoIFNα, low pH and detergent stability; Mω of 18.000 Dalton, binding to poly- or monoclonal homologous antibodies or IFNα receptors and on the antiviral activity.

Using a combination of extraction, differential precipitation, size and affinity chromatography methods bacterial BoIFNα was purified to a high specific activity. The purified IFNα preparations showed antiviral activity on a large spectrum of different eukaryotic cells from human to lower mammalia. The BoIFNα has a specially high activity in cells of bovine origin.

EXAMPLE

Stage 1

Isolation of High Molecular Weight DNA from Calf Liver

The source of DNA for the genomic library was the liver of a freshly slaughtered Holstein Friesian cow. DNA was prepared essentially according to Blin & Stafford (Nucleic Acid Res. 3 9 1976), 50 gr of frozen tissue were ground to a thin powder in a Waring blendor in the presence of liquid nitrogen. The powder was added in small amounts to a solution of 400 ml phenol and 400 ml extraction buffer (20 mM tris-HCl pH 7.6, 0.5% SDS, 1.0M NaCl; 1 mM EDTA). The mixture was stirred on a magnetic stirrer for 30 min. and then centrifuged at 4000 rpm for 10 min. in a Sorvall GSA rotor.

The aqueous phase was reextracted with phenol and then with ether in a separatory funnel.

The DNA preparation was placed in a dialysis bag and RNase (free of DNase) was added to make a final concentration of 50 μg/ml. Dialysis was carried on overnight at room temperature versus 10 liter of 20 mM Tris-HCL pH 7.6, 10 mM NaCl and 1 mM EDTA.

EDTA (50 mM final concentration), SDS (0.5% final) and proteinase K (100 μg/ml final) were added to the DNA solution which was incubated for 3 h. at 37° C.

DNA was phenol extracted twice, ethanol precipitated and resuspended in 10 mM Tris-HCl pH 7.6, 1 mM EDTA (TE buffer).

Stage 2

Preparation of 16 kb DNA Fragments from partially digested Calf Liver DNA.

16 kb bovine DNA fragments were obtained by partial digestion of high molecular weight DNA with the restriction enzyme Sau 3A.

The enzyme recognizes the 4 bp sequence GATC and generates a 4 b cohesive end. The GATC end is homologous to the one generated by the restriction enzyme BamH 1. BamH 1 will be used later on to obtain the left and right arms of λL47.1 vector, which will be ligated to the bovine DNA. 400 μg of high molecular weight calf liver DNA was digested with 100 units of Sau3A. After incubation at 37° C. for 1 hour the reaction was stopped by adding phenol. The DNA was extracted twice with phenol/chloroform, precipitated in ethanol and dissolved in TE buffer.

To fractionate the DNA, the preparation was heated 10 minutes at 68° C., chilled to 20° C. and layered on a 38 ml 10–40% sucrose gradient in 1M NaCl 20 mM Tris-HCl pH 8.0 and 5 mM EDTA. Centrifugation was performed at 26.000 rpm in a Beckman SW 27 rotor for 24 hrs at 20° C. 0.5 ml fractions were collected, 10 μl aliquots were analyzed by electrophoresis through an 0.8% agarose gel. Following electrophoresis gradient fractions containing DNA in the 12–18 kb size range were pooled.

At this stage, it was found that it is impossible to precipitate the DNA. It turned out that both dialysis and a concentration step are required prior to precipitation. Dialysis was performed against 4 liters of TE overnight. Concentration was achieved by chromatography on DEAE cellulose. The dialysed fractions (8 ml) were loaded on an 0.3 ml column of DE-52 pre-equilibrated with 0.1M NaCl 0.01M Tris-HCl pH 7.6. The column was then washed with several column volumes of the equilibration buffer. The bound DNA was then eluted with 6.5M urea, 1M NaCl and 10 mM Tris-HCl pH 7.6. 0.5 ml fractions were collected and the ones containing DNA were pooled, precipitated and dried in vacuum.

Dried out pellets of high molecular weight DNA are hard to dissolve. Complete resuspension in TE at a concentration of 1 μg/μl was achieved by 4 hours incubation at room temperature. 400 μg of chromosomal liver DNA yielded 60 μg of purified 12–18 kb DNA fragments.

Stage 3

Preparation of Bacteriophage λL47.1 DNA

Bacteriophage λL47, designed by Leonen and Brammar, (Gene 10 p. 249 1980) was used as a cloning vector for the construction of the genomic library. DNA was prepared from a phage suspension containing $10^{13}$ CsCl purified particles. CsCl was removed by dialyzing the suspension twice against a 1000 fold volume of 50 mM Tris-HCl pH 8.0, 10 mM NaCl and 10 mM MgCl$_2$.

After two hours, the phages were removed from the dialysis bag, EDTA (final concentration 20 mM) SDS (final concentration 0.5%) and proteinase K (50 μg/ml) were added and the preparation was incubated for 1 hr. at 65° C. This was followed by consecutive extraction with phenol, phenol/chloroform and chloroform.

Stage 4

Preparation of "λ Arms"

The bacteriophage λ vectors require that the middle "stuffer segment" of their genome is removed in order to accommodate for 15–20 kb of the foreign DNA. This process is generally referred to as the "preparation of the arms". In the case of λL47 this is achieved by digestion of the phage DNA with the restriction enzyme BamH 1 followed by sucrose density gradient centrifugation. 3 fragments are generated by this treatment:

A 23.5 kb fragment representing the left arm, a 10.5 kb fragment representing the right arm, and a 6.6 kb stuffer fragment.

Quantitative separation of arms and stuffer fragment were obtained by annealing the right and left arms of the vector through their cohesive ends (under conditions where the ends created by restriction digest are not annealed) to form a 34 kb fragment prior to the sucrose density gradient separation. In addition, the stuffer fragment was further reduced in size by enzymes which cleave this fragment exclusively. In the case of L47.I Xho I and Sal I were the enzymes used to produce fragments smaller than 4.3 kb.

Procedure:

150 μg of bacteriophage DNA were digested with a three fold excess of Bam H I. Upon completion of Bam H I digestion the DNA was treated with Sal I and Xho I.

The digested DNA was extracted twice with phenol/chloroform, ethanol precipitated and resuspended at a concentration of 150 μg/ml. To anneal the left and right arms $MgCl_2$ was added to a concentration of 10 mM and the preparation was incubated at 42° C. for 1 hour. The digested and annealed DNA was loaded on 38 ml 10–40% sucrose gradients containing 20 mM Tris HCl pH 7.6, 1M NaCl and 5 mM EDTA. No more than 60 μg of DNA were applied on one gradient. Centrifugation was performed in a SW 27 rotor at 26,000 rpm for 24 hours at 15° C. 0.5 ml fractions were collected and 20 μl aliquots from each fraction were analyzed by gel electrophoresis. Fractions containing equimolar amounts of left and right arms were pooled, dialyzed and concentrated as described for fragmented calf liver DNA.

Three gradients loaded with 50 μg digested DNA yielded 45 μg of purified arms.

Stage 5

Ligation, Packaging and Amplification

10 μg of arms were ligated to 2.5 μg of insert in a total volume of 100 μl in the presence of 60 mM Tris-HCl pH 8.0, 10 mM $MgCl_2$, 1 mM ATP, 15 mM DTT and 1000 units of T4 ligase (N.E. iolabs).

The reaction was performed in two steps. First, the arms were mixed with Tris buffer and $MgCl_2$ and incubated for 1 hour at 42° C. to let annealing of the λ cohesive ends, then ATP, DTT, bovine DNA and ligase were added and the reaction was transferred to 14° C. for 16 hours. A λ packaging mixture prepared essentially according to the method of Hohn B (Methods in Enzymology 68 p. 299, 1979) was used.

1 μg of ligated DNA yielded $7 \times 10^5$ pfu. To prepare a complete library, 4 μg of ligated DNA were used resulting in a primary library of $2.8 \times 10^6$ phages.

The genomic library was amplified by propagating the bateriophages in *E. coli* LE 392 on NZCYM plates (1% NZ amine, 0.5% yeast extract, 0.1% casamino acid, 0.2% $MgSO_4$ and 1% Agar). Aliquots of the packaging mixture containing recombinant bacteriophages were mixed with bacteria and incubated at 37° C. for 20 minutes. Melted top agar (NZCYM+0.5% Agar) was added and the suspension was spread onto 150 mm plates of NZCYM agar. Each plate was overlaid with 7 ml of top agar containing 17,000 recombinant bacteriophages and 0.2 ml host bacteria. Batches of 30 plates were prepared at a time. A total of 150 plates were used to amplify the library. Plates were incubated at 37° C. for 9 hours.

To collect the bacteriophages, top agars were pooled into a sterile beaker. Chloroform was added to a final concentration of 5% and the lysates were incubated for 15 minutes at room temperature with occasional shaking. The suspension was then left overnight at 4° C. to allow elution of bacteriophages. Cell debris and agar were then removed by centrifugation at 4° C. for 15 minutes.

The total number of bacteriophages in the amplified library was about $8 \times 10^{12}$ pfu. This indicates an amplification of $2.5 \times 10^6$ over the primary library.

Stage 6

Determination of Hybridization Conditions between the HuIFN-α gene and Bovine Sequences.

To determine whether or not the HuIFN-α sequences can be used to probe the bovine genomic library, we prepared genomic blots of bovine DNA and various labelled fragments of the HuIFN-αJl gene. (Shafferman A. et al. patent application No. 70678). The HuIFN-α gene was spliced by Sau 3A into 4 fragments of 177, 207, 270 and 515 bp and the isolated fragments were labelled by nick translation with α $32_P$ dATP and hybridized under various hybridization conditions to the bovine genomic blots.

Using the fragment Sau3A 177 (this fragment covers the N terminal region of the coding block) several distinct bands were revealed. This fragment was chosen as the probe for screening the library.

Stage 7

Screening of the Genomic Library for Interferon Sequences.

The genomic library was plated on 150 mm Petri dishes at a concentration of 30,000 bacteriophage particles per plate. 3o plates were used, each plate was prepared according to the following procedure: 50 μl of bacteriophage suspension were mixed with 0.2 ml of an *E. coli* LE 392 overnight culture and incubated for 20 minutes at 37° C., then 7 ml of top agarose (0.7% agarose in NZYCM Medium) were added and the mixture was poured onto a dry plate containing NZYCM+1.5% agar.

The plates were incubated at 37° C. until the plaques reached a diameter of 1 mm (about 7 hours) and then chilled for 1 hour at 4° C. to allow the top agarose to harden.

The plaques were transferred to nitrocellulose circles by placing the filters on top of the soft agar for 10 minutes. The filters were then peeled off and floated on top of a denaturing solution made of 1.5M NaCl and 0.5M NaOH for 30 seconds. The filters were then dipped into the solution for another 30 seconds and transferred to the neutralizing solution (1.5M NaCl, 0.5M Tris HCl ph/8 for 5 minutes. The filters were rinsed in $2 \times SSC$, dried at room temperature and baked at 80° C. under vacuum for 2 hours.

The filters were first thoroughly wetted in $6 \times SSC$ and then transferred to a tray containing 300 ml washing solution. (50 mM Tris HCl, pH-8.0, 1M NaCl, 1 mM EDTA, 0.1% SDS), and incubated at 42° C. with constant agitation. After 2 hours the filters were removed and transferred to a dish containing 100 ml prehybridizing solution (50% deionized formamide, $5 \times$ Denhardt's solution, $6 \times SSC$, 0.5% SDS and 100 μg/ml denatured Salmon Sperm DNA).

Prehybridization was carried on for 4 hours and then heat denatured $^{32}P$ labeled DNA probe (Sau3A 177 fragment) was added directly to the prehybridization solution. After 48 hours of hybridization at 42° C., the filters were washed in $2 \times SSC$, 0.1% SDS.

The washing procedure consisted of three, 15-minute washes at room temperature, followed by two 1.5-hour washes at 42° C.

The filters were dried and exposed to an X-ray film. 13 hybridization spots were identified.

Phages from each spot were plated and rehybridized to the 177 bp probe, and at that stage it was found that clones 105, 116 and 120 hybridized to a lesser extent than clones 103, 107, 108, 111, 115, 118, while remaining clones did not rehybridize to the probe. The clones which rehybridized were further purified. The λ DNA was isolated and subjected to digestion with Bam HI, Hind III and EcoR I, blotted to nitrocellulose filter and hybridized again to the HuIFNα 177 bp probe as well as to the HuIFN α 270 and 515 bp probes. Any clone that hybridizes to each of the 3 probes is a good candidate for carrying a BoIFNα sequence. Out of the 9 clones tested, 6 hybridized with each of the 3 probes. The clones which did not hybridize with either the 270 bp and the 515 bp were the same clones which hybridized weakly with the 177 bp probe in our initial screening procedure.

In conclusion, clones 103, 107, 108, 111, 115 and 118 are candidates to carry a substantial part of the BoIFNα sequences.

Stage 8

Localization of Interferon Sequences on the λ Hybrid DNA

Hind III, BamH I, EcoR I and Sal I restriction maps of clones 103, 107, 108, 111, 115 and 118 were determined by multiple enzyme digests. As can be judged from these maps, clones 115 and 118 represent overlapping regions on the bovine chromosome.

To localize the BoIFN sequences, blots of each of the clones digested with the restriction enzymes mentioned above were incubated separately with each of the 3 Sau3A probes of HuIFNα (177 bp, 270 bp, and 515 bp). Altogether, it can be concluded that from the restriction and hybridization studies, that at least 5 distinct IFNα genes are present in the bovine genome.

Clones 103, 107, 108 and 115 were further characterized. DNA fragmnets carrying the entire hybridizing block for each of these clones were isolated and subcloned into the Hind III site of the plasmid pBR322 and then sequenced by the method of Maxam and Gilbert (Proc. Nat. Acad. Sci. 74 p. 560, 1977). Plasmids carrying the genomic inserts of interest was subjected to cleavage with appropriate restriction enzymes. DNA fragments were labeled with ($\alpha$-$^{32}$p) deoxynucleotides using the large fragment of E. coli DNA Polymerase I.

The genes carried on clones 103, 108, 115 and 107 were designated BoIFN-αA, BoIFN-αB, BoIFN-αC and BoIFN-αD respectively. The sequence of the gene BoIFN-αA is shown in FIG. 1. The sequence of the gene BoIFNα-B is shown in FIG. 2, the sequence of gene BoIFN-αC is shown in FIG. 3, and the sequence of gene BoIFN-αD is shown in FIG. 4.

The four sequences contain an open reading frame of 570 bp encoding for 189 amino acids. The 23 first amino acids of the putative polypeptide is the signal peptide characteristics of IFNα molecules. The putative mature proteins are very closely related (FIG. 5), their amino acid sequence is highly conserved with an average homology of 93%. It should be noted that all four polypeptides resemble human IFNαs. The homology between the putative amino acid sequence of the BoIFN and that of the consensus human IFNα (Goeddel D. U. et al, 1981 Nature 290.20) is in the order of 65%.

Stage 9

Preparation of Expression Vehicle

To show that BoIFNα genes have biological activity, it was required to produce this protein and thus efficient expression vehicles were designed for the production of the IFNα polypeptide.

Figure 6:
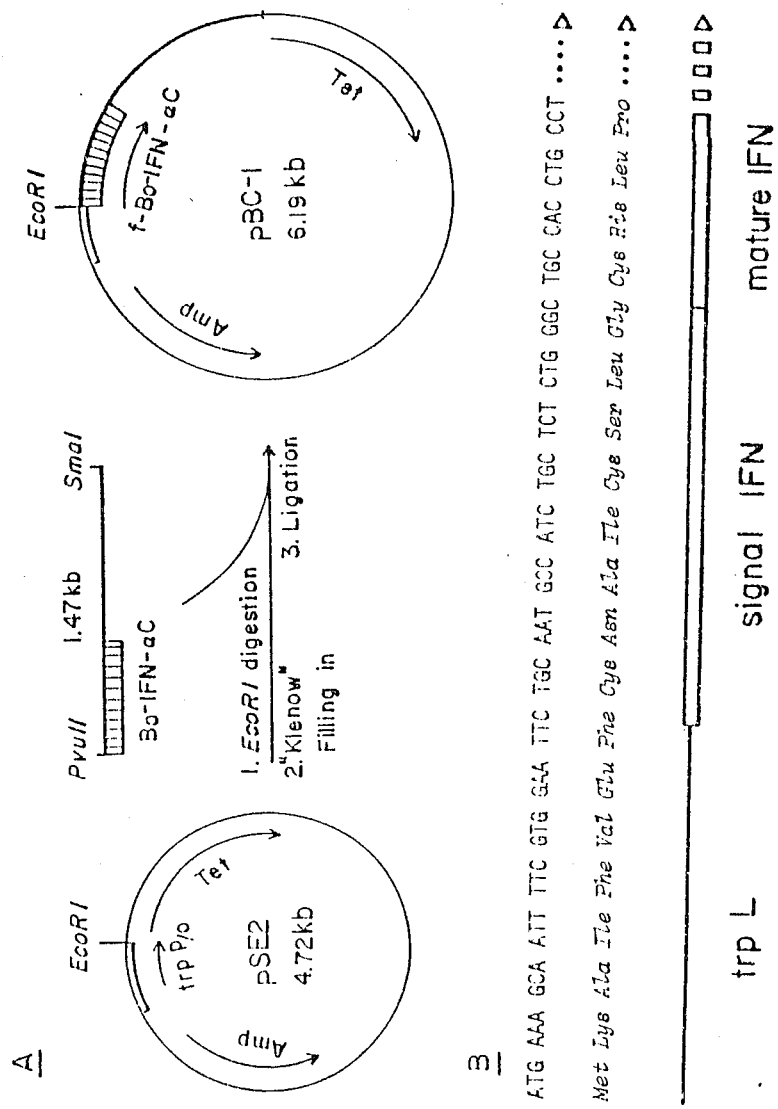
FIG. 6 illustrates the construction of a recombinant plasmid expressing a fused BoIFN-α C polypeptide.

Here we describe the use of one such vehicle pSE2-in which the E. coli trp sequences serve as the expression element. This trp promoter plasmid belongs to a family of trp expression vehicles described previously (Rose Shafferman 1981 PNAS 78 6670; Shafferman et al. J. Mol. Biol. 161 57; Grosfeld et al. 1984 M.G.G. 195, 358; Interferon production, patent application No. 70678, 1984).

pSE2 has a unique EcoR 1 site located within the 6th codon of the trp L. pSE2 was digested with EcoR I and the cohesive ends were filled in by DNA polymerase I large fragment. This DNA was ligated to the PvuIII-Sma I fragment of clone 115 containing the entire coding block of the mature BoIFNα-C as well as 24 bp coding for part of the signal peptide plasmids containing the BoIFNα-C DNA fragment in th appropriate orientation were isolated and analyzed to verify a correct fusion of trp L sequences with bovine IFN sequences. This plasmid was designated pBC-l (FIG. 6).

Different trp expression vehicles such as pHG5 (Grosfeld et al. 1984 M.G.G. 195, 358) were used to produce a mature met-IFN-α polypeptide taking advantage of the single Cla I site in pHG5 and the Fnu4HI site at position 154 of the BoIFN-αC sequence (FIG. 7).

Plasmids carrying the various BoIFN derivatives including those coding for the met-mature BoIFN such as pBC-3 (FIG. 7) were used to transform different E. coli strains.

Stage 10

Production and Purification of a BoIFN-αC Polypeptide Derivative:

Here we describe the production and purification of BoIFNα-C derivative polypeptides coded by pBC-1 or pBC-3.

E. coli LE392 cells harboring pBC-1 or pBC-3 were grown to a density of $8\times10^8$ cells/ml in L medium supplemented with 0.5% K$_2$HPO$_4$ and 0.2% KH$_2$PO$_4$.

Bacterial extract containing BoIFN-αC was submitted to 60 minutes centrifugation at 28.000 rpm in an R-30 Beckman rotor and the supernatant was collected. Proteins were precipitated by 7.5% TCA. The precipitate was resuspended in 0.1M K-phosphate buffer pH 8.0 and the nonsoluble proteins were removed by centrifugation. The clear supernatant was applied directly to a monoclonal affinity column. A commercially available column (Serono Diagnostic #23-4), containing monoclonal antibodies against HuIFN-α (34) was found to be suitable for the purification of BoIFN-αC. Following application, the column was washed with several volumes of 0.3M NaCl in 0.1M K phosphate buffer pH 8.0 and the IFN was eluted with 0.3M NaCl in 0.1M acetate buffer pH 2.4. The capacity of the column is $5\times10^6$ BoIFN units per 1 ml of column material. A 200 fold purification was achieved with a recovery of 50%; the specific activity of the thus obtained preparation was about $2\times10^8$ units/mg protein. The BoIFN-αC preparation seems to be homogenous as judged by SDS-PAGE.

Stage 11

Characterization of Genetically Engineered BoIFNα Products:

The purified BoIFNα polypeptide derivatives were tested for biological antiviral activity by the CPE method using as a challenge VSV.

Tests were performed on the following cells:
Human—HeLa and FS11
Monkey—Vero
Bovine—MDBK and EBtr
Rodent—L929 and BHK.
Pronounced antiviral activity was observed on the bovine lines.

Immunological Properties:

a. The antiviral activity of the bacterial IFNα was neutralized by anti-human IFN-α or by anti-human IFN-β. However, BoIFNα-C was shown to share antigenic determinants with HuIFNαs by binding experiments to immobilized anti-human α Interferon.

Physicochemical Properties:

a. stable to pH 2 for 2 hours. 37° C.
b. stable to SDS 0.1% with half-life time longer than 5 hours.
c. The IFNα polypeptide migrates on SDS-polyacrylamide gels at a position equivalent to molecular weight of ~18.000.

The enclosed Figures define the DNA sequences coding for the products of the invention and also the composition of the bovine type interferons of the invention.

FIG. 1

CTGAAGGAAGGTCTTCAGAGAACCTAGAGAGCAGGTTCACAGAGTCACCCACCTCACCAG

GCCAAAGCATCTGCAAGGTCCCCGATGGCCCCAGCCTGGTCCTTCCTGCTATCCCTGTTG
                 MetAlaProAlaTrpSerPheLeuLeuSerLeuLeu

▽

CTGCTCAGCTGCAACGCCATCTGCTCTCTGGGTTGCCACCTGCCTCACACCCACAGCCTG
LeuLeuSerCysAsnAlaIleCysSerLeuGlyCysHisLeuProHisThrHisSerLeu

GCCAACAGGAGGGTCCTGATGCTCCTGCAACAACTGAGAAGGGTCTCCTTCCTCCTGC
AlaAsnArgArgValLeuMetLeuLeuGlnGlnLeuArgArgValSerProSerSerCys

CTGCAGGACAGAAATGACTTCGAATTCCTCCAGGAGGCTCTGGGTGGCAGCCAGTTGCAG
LeuGlnAspArgAsnAspPheGluPheLeuGlnGluAlaLeuGlyGlySerGlnLeuGln

AAGGCTCAAGCCATCTCTGTGCTCCACGAGGTGACCCAGCACACCTTCCAGCTCTTCAGC
LysAlaGlnAlaIleSerValLeuHisGluValThrGlnHisThrPheGlnLeuPheSer

ACAGAGGGCTCGCCCGCCACGTGGGACAAGAGCCTCCTGGACAAGCTACGCGCTGCGCTG
ThrGluGlySerProAlaThrTrpAspLysSerLeuLeuAspLysLeuArgAlaAlaLeu

GATCAGCAGCTCACTGACCTGCAAGCCTGTCTGACGCAGGAGGAGGGGCTGCGAGGGGCT
AspGlnGlnLeuThrAspLeuGlnAlaCysLeuThrGlnGluGluGlyLeuArgAlyAla

CCCCTGCTCAAGGAGGACTCCAGCCTGGCTGTGAGGAAATACTTCCACAGACTCACTCTC
ProLeuLeuLysGluAspSerSerLeuAlaValArgLysTyrPheHisArgLeuThrLeu

TATCTGCAAGAGAAGAGACACAGCCCTTGTGCCTGGGAGGTTGTCAGAGCAGAAGTCATG
TyrLeuGlnGluLysArgHisSerProCysAlaTrpGluValValArgAlaGluValMet

AGAGCCTTCTCTTCCTCAACAAACTTGCAGGAGAGTTTCAGGAGAAAGGACTGACACACA
ArgAlaPheSerSerSerThrAsnLeuGlnGluSerPheArgArgLysAspEND

CCTGGTCCAACACGGAAA

FIG. 2

TGAACCCATTTGGAGAGTGCAAGCTGAAACGCAAAAACAAAAGT

AGAAAACAAGAGGGAACTTTCACAAAGTGGAAACCATGGGCTCCTATTTAAGACACAGGC

CTGAAGGAAGGTCTTCAGAGAATCTAGAGAGCAGGTTCACAGAGTCACCCACCGCCCGAG

GCCAAAGCCTCTGCAAGGTCCCCGATGGCCCCAGCCTGGTCCTTCCTCCTAGCCCTGCTG
                 MetAlaProAlaTrpSerPheLeuLeuAlaLeuLeu

▽

CTGCTCAGCTGCAACGCCATCTGCTCTCTTTGGGTTGCCACCTGCCTCACACCCACAGCCTG
LeuLeuSerCysAsnAlaIleCysSerLeuGlyCysHisLeuProHisThrHisSerLeu

CCCAACAGGAGGGTCCTGACACTCCTGCGACAACTGAGGAGGGTCTCCCCTTCCTCCTGC
ProAsnArgArgValLeuThrLeuLeuArgGlnLeuArgArgValSerProSerSerCys

CTGCAGGACAGAAATGACTTTGCATTCCCCCAGGAGGCGCTGGGTGGCAGCCAGTTGCAG
LeuGlnAspArgAsnAspPheAlaPheProGlnGluAlaLeuGlyGlySerGlnLeuGln

AAGGCTCAAGCCATCTCTGTGCTCCACGAGGTCACCCAGCACACCTTCCAGCTCTTCAGC
LysAlaGlnAlaIleSerValLeuHisGluValThrGlnHisThrPheGlnLeuPheSer

ACAGAGGGCTCGGCCACTACGTGGGACGAGAGCCTCCTGGACAAGCTCCACGCTGCACTG
ThrGluGlySerAlaThrThrTrpAspGluSerLeuLeuAspLysLeuHisAlaAlaLeu

GATCAGCAGCTCACTGACCTGCAAGCCTGTCTGAGGCAGGAGGAGGGGCTGCGAGGGGCT
AspGlnGlnLeuThrAspLeuGlnAlaCysLeuArgGlnGluGluGlyLeuArgGlyAla

CCCCTGCTCAAGGAGGGTTCCAGCCTGGCTGTGAGGAAATACTTCCACAGACTCACTCTC
ProLeuLeuLysGluGlySerSerLeuAlaValArgLysTyrPheHisArgLeuThrLeu

TATCTGCAAGAGAAGAGACACAGCCCTTGTGCCTGGGAGGTTGTCAGAGCAGAAGTCATG
TyrLeuGlnGluLysArgHisSerProCysAlaTrpGluValValArgAlaGluValMet

AGAGCCTTCTCTTCTTCAACAAACTTGCAGGAGAAATTCAGGAGAAAGGACTGACACACA
ArgAlaPheSerSerSerThrAsnLeuGlnGluLysPheArgArgLysAspEND

CCTGGTTCAACATGGAAA

AGAAAGCAAGAGGGAACTTTCAGAAAATGGAAACCATGGGCTCCTATTTAACACACAGGC   FIG. 3

CTGAAGGAAGGTCTTCAGAGAACCTAGAAAGCAGGTTCACAGAGTCACCCACCTCCCCAG

GCCACAGCATCTGCAAGGTCCCCAATGGCCCCAGCCTGGTCCTTCCGCCTGGCCCTGCTG
                                        MetAlaProAlaTrpSerPheArgLeuAlaLeuLeu
                                        ▽
CTGCTCAGCTGCAATGCCATCTGCTCTCTGGGCTGCCACCTGCCTCACACCCACAGCCTG
LeuLeuSerCysAsnAlaIleCysSerLeuGlyCysHisLeuProHisThrHisSerLeu

GCCAACAGGAGGGTCCTGATGCTCCTGGGACAACTGAGGAGGGTCTCCCCTTCCTCCTGC
AlaAsnArgArgValLeuMetLeuLeuGlyGlnLeuArgArgValSerProSerSerCys

CTGCAGGACAGAAATGACTTTGCATTCCCCCAGGAGGCGCTGGGTGGCAGCCAGTTGCAG
LeuGlnAspArgAsnAspPheAlaPheProGlnGluAlaLeuGlyGlySerGlnLeuGln

AAGGCTCAAGCCATCTCTGTGCTCCACGAGGTGACCCAGCACACCTTCCAGCTTTTCAGC
LysAlaGlnAlaIleSerValLeuHisGluValThrGlnHisThrPheGlnLeuPheSer

ACAGAGGGCTCGGCCACCATGTGGGATGAGAGCCTCCTGGACAAGCTCCGCGATGCACTG
ThrGluGlySerAlaThrMetTrpAspGluSerLeuLeuAspLysLeuArgAspAlaLeu

GATCAGCAGCTCACTGACCTGCAATTCTGTCTGAGGCAGGAGGAGGAGCTGCAAGGAGCT
AspGlnGlnLeuThrAspLeuGlnPheCysLeuArgGlnGluGluGluLeuGlnGlyAla

CCCCTGCTCAAGGAGGACTCCAGCCTGGCTGTGAGGAAATACTTCCACAGACTCACTCTC
ProLeuLeuLysGluAspSerSerLeuAlaValArgLysTyrPheHisArgLeuThrLeu

TATCTGCAAGAGAAGAGACACAGCCCTTGTGCCTGGGAGGTTGTCAGAGCACAAGTCATG
TyrLeuGlnGluLysArgHisSerProCysAlaTrpGluValValArgAlaGlnValMet

AGAGCCTTCTCTTCCTCAACAAACTTGCAGGAGAGTTTCAGGAGAAAGGACTGACACACA
ArgAlaPheSerSerSerThrAsnLeuGlnGluSerPheArgArgLysAspEND

CCTGGTTCAACACGGAAATGATTCTCATGGACCAACAGACCACACTTCCTCCTGCGCTGC

CATGTGGAAGATTCATTTCTGCTGTCATCAGGCACTGAACTGAATCAATTTGTTAAATGA

AGAAAGCAAGAGGGAACTTTCAGAAAATGGAAACCATGGACTCCTATTTAAGACACAGAC   FIG. 4

CTGAAGGAAGGTCTTCAGAGAACCTAGAAAGCAGGTTCACAGAGTCACCCACCGCCCCAG

GCCACAGCCACTTCAAGGTCCCCGATGGCCCCAGCCTGGTCCCTCCTCCTGGCTCTGCTG
MetAlaProAlaTrpSerLeuLeuLeuAlaLeuLeu
                                        ▽
CTGCTCAGCTGCAACGCCATCTGCTCTCTGGGCTGCCACCTGCCTCACTCCCACAGCCTG
LeuLeuSerCysAsnAlaIleCysSerLeuGlyCysHisLeuProHisSerHisSerLeu

GCCAAGAGGAGAGTCCTGACACTCCTGCGACAACTGAGGAGGGTCTCCCCTTCCTCCTGC
AlaLysArgArgValLeuThrLeuLeuArgGlnLeuArgArgValSerProSerSerCys

CTGCAGGACAGAAATGACTTCGCATTCCCCCAGGAGGCGCTGGGTGGCAGCCAGTTGCAG
LeuGlnAspArgAsnAspPheAlaPheProGlnGluAlaLeuGlyGlySerGlnleuGln AAGGCTCAAGCCATCTCTGTACTCCACGAGGTGACCCAACACACCTTCCAGCTTTCCAGC
LysAlaGlnAlaIleSerValLeuHisGluValThrGlnHisThrPheGlnLeuSerSer ACAGAGGGCTCGGCCGCTGTGTGGGATGAGAGCCTCCTGGACAAGCTCCGCACTGCACTG
ThrGluGlySerAlaAlaValTrpAspGluSerLeuLeuAspLysLeuArgThrAlaLeu GATCAGCAGCTCACTGACCTGCAAGCCTGTCTGAGGCAGGAGGAGGGGCTGCCAGGGGCT
AspGlnGlnLeuThrAspLeuGlnAlaCysLeuArgGlnGluGluGlyLeuProGlyAla CCCCTGCTCAAGGAGGACTCCAGCCTGGCTGTGAGGAAATACTTCCACAGACTCACTCTC
ProLeuLeuLysGluAspSerSerLeuAlaValArgLysTyrPheHisArgLeuThrLeu TATCTGCAAGAGAAGAGACACAGCCCTTGTGCCTGGGAGGTTGTCAGAGCACAAGTCATG
TyrLeuGlnGluLysArgHisSerProCysAlaTrpGluValValArgAlaGlnValMet -continued AGAGCCTTCTCTTCCTCAACAAACTTGCAGGAGAGATTCAGGAGAAAGGACTGACACACA
ArgAlaPheSerSerSerThrAsnLeuGlnGluArgPheArgArgLysAspEND

CCTGGTTCAACACGGAAATGATTCTCACGGACCAACAGACCACACTTCCTCCTGCGCTGC

CATGTGGAAGACTCATTTCTGCTGTCATCAGGCACTGAACTGAATCAATTTGTTAATGGT

FIG. 5

```
              S1              S20     1                  20                      40
BoIFN- C   MAPAWSFRLALLLLSCNAICSLGCHLPHTHSLANRRVLMLLCQLRRVSPSSCLQDRNDFAFPQ
BoIFN- A             L S                               Q                      E L
BoIFN- B             L              S  P             T  R
BoIFN- D             LL                  K           T  R 60                  80                   100
BoIFN- C   EALGGSQLQKAQAISVLHEVTQHTFQLFSTEGSATMWDESLLDKLRDALDQQLTDLQFCLRQE
BoIFN- A                                   PAT   K        A          A T
BoIFN- B                                    T              HA         A
BoIFN- D                            S       AV             T          A 120                 140                  160
BoIFN- C   EELQGAPLLKEDSSLAVRKYFHRLTLYLQEKRHSPCAWEVVRAQVMRAFSSSTNLQESFRRKD
BoIFN- A     G R                                 E
BoIFN- B     G R       G                         E                    K
BoIFN- D     G P                                                      R
```

We claim:

1. A genetically engineered bovine interferon of the IFN-α-type which is pre-BoIFN-α A, mature BoIFN-α A and Met-mat-BoIFn-α A defined by the amino acid sequence with a methionine codon preceding the Cys codon, as shown in FIG. 1.

2. The interferon as to claim 1 which has the following characteristics:
   affords protection to bovine cells against viral infections;
   links to immobilized anti-HuIFn-antibodies;
   is stable at pH 2 and 37° C. for at least 2 hours; is stable to SDS 0.1% with a half-life longer than 5 hours;
   migrates on SDS polyacrylamide gels at a position equivalent to a molecular weight of about 18,000 daltons.

3. The genetically engineered bovine interferon of the IFN-α-type which is, pre-BoIFN-α B, mature BoFIN-α-B and Met-mature-BoIFN-α-B as defined by the amino acid sequence shown in FIG. 2 hereinbelow with a methionine codon preceding the Cys codon.

4. The bovine genetically engineered interferon of the α-type as claimed in claim 3, having the following characteristics:
   affords protection to bovine cells against viral infections;
   links to immobilized anti-HuIFN-antibodies;
   is stable at pH 2 and 37° C. for at least 2 hours;
   is stable to SDS 0.1% with a half-life longer than 5 hours;
   migrates on SDS polyacrylamide gels at a position equivalent to a molecular weight of about 18,000 daltons.

5. The genetically engineered bovine interferon of the IFN-α-type pre-BoIFN-α C, mature BoIFN-α C and Met-mature BoIFN-α C as defined by the aminoacid sequence shown in FIG. 3 with a methionine codon preceding the Cys codon.

6. The bovine genetically engineered interferon of the α-type as claimed in claim 5, having the following characteristics:
   affords protection to bovine cells against viral infections;
   links to immobilized anti-HuIFN-antibodies;
   is stable at pH 2 and 37° C. for at least 2 hours;
   is stable to SDS 0.1% with a half-life longer than 5 hours;
   migrates on SDS polyacrylamide gels at a position equivalent to a molecular weight of about 18,000 daltons.

7. A polypeptide having bovine interferon activity, produced from a DNA or a cloning vehicle which includes DNA encoding BoIFN-α A as defined in claim 1.

8. A polypeptide having bovine interferon activity produced from a DNA or a cloning vehicle which includes DNA encoding BoIFN-α B as defined in claim 3.

9. A polypeptide having bovine interferon activity produced from a DNA or a cloning vehicle which includes DNA encoding BoIFn-α C as defined in claim 5.

10. The polypeptide BoIFN-α A according to claim 1 produced by culturing a cell which is a procaryotic or a eucaryotic cell under conditions permitting expression of the DNA encoding the BoIFN-α A and recovering said polypeptide from the reaction mixture.

11. The polypeptide BoIFN-αB according to claim 3 produced by culturing a cell which is a procaryotic or a eucaryotic cell under conditions permitting expression of the DNA encoding the BoIFN-αB and recovering said polypeptide from the reaction mixture.

12. The polypeptide BoIFN-αC according to claim 5 produced by culturing a cell which is a procaryotic or a eucaryotic cell under conditions permitting expression of the DNA encoding the BoIFN-αC and recovering said polypeptide from the reaction mixture.

* * * * *